(12) United States Patent
Rose et al.

(10) Patent No.: US 12,397,126 B2
(45) Date of Patent: Aug. 26, 2025

(54) DIFFUSER FOR A COMPONENT OF A RESPIRATORY THERAPY SYSTEM

(71) Applicant: Fisher & Paykel Healthcare Limited, Auckland (NZ)

(72) Inventors: Hamish Joshua Rose, Auckland (NZ); Nigel Trinidade, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 1093 days.

(21) Appl. No.: 17/309,381

(22) PCT Filed: Nov. 26, 2019

(86) PCT No.: PCT/NZ2019/050154
§ 371 (c)(1),
(2) Date: May 24, 2021

(87) PCT Pub. No.: WO2020/111951
PCT Pub. Date: Jun. 4, 2020

(65) Prior Publication Data
US 2022/0023569 A1    Jan. 27, 2022

Related U.S. Application Data

(60) Provisional application No. 62/771,444, filed on Nov. 26, 2018.

(51) Int. Cl.
*A61M 16/06*    (2006.01)
*A61M 16/08*    (2006.01)

(52) U.S. Cl.
CPC .... *A61M 16/0633* (2014.02); *A61M 16/0825* (2014.02); *A61M 2202/0225* (2013.01); *A61M 2205/0216* (2013.01); *A61M 2205/42* (2013.01)

(58) Field of Classification Search
CPC ....... A61B 5/0836; A61B 5/087; A61B 5/097; A61B 5/6803; A61M 11/00; A61M 15/00;
(Continued)

(56) References Cited

U.S. PATENT DOCUMENTS 4,454,881 A    6/1984   Huber et al.
4,616,647 A    10/1986   McCreadie
(Continued)

FOREIGN PATENT DOCUMENTS

AU    2008244578    12/2011
AU    2017201346    7/2018
(Continued)

OTHER PUBLICATIONS

International Search Report and Written Opinion of PCT/NZ2019/050154, Dated Feb. 17, 2020, in 19 pages.

*Primary Examiner* — Annette Dixon
(74) *Attorney, Agent, or Firm* — VIA LLP

(57) ABSTRACT

This disclosure provides a mask assembly for respiratory therapy, comprising: a vent for exhausting gas flow from an interior of the mask assembly, the vent comprising at least one vent hole; and a diffuser material defining a diffusing area sufficient to cover the vent hole and having a periphery. A region of the diffusing area of the diffuser material includes a localised joint region in which multiple fibres of the diffuser material are bonded or interlocked together. The location of the localised joint region is offset from the vent hole. Further embodiments are disclosed in which the shape of the diffusing material matches the shape of a vent hole array, or has other properties related to the vent hole array or the shape or other features of the vent.

23 Claims, 8 Drawing Sheets

(58) Field of Classification Search
CPC ............... A61M 15/08; A61M 15/085; A61M 16/0051; A61M 16/0057; A61M 16/0066; A61M 16/009; A61M 16/0093; A61M 16/024; A61M 16/044; A61M 16/0463; A61M 16/06; A61M 16/0605; A61M 16/0611; A61M 16/0616; A61M 16/0622; A61M 16/0627; A61M 16/0666; A61M 16/0683; A61M 16/0694; A61M 16/08; A61M 16/0816; A61M 16/0825; A61M 16/0833; A61M 16/085; A61M 16/0866; A61M 16/0875; A61M 16/10; A61M 16/1045; A61M 16/105; A61M 16/1055; A61M 16/1065; A61M 16/107; A61M 16/14; A61M 16/16; A61M 16/161; A61M 16/20; A61M 16/208; A61M 16/22; A61M 2016/0021; A61M 2016/0027; A61M 2016/003; A61M 2016/0033; A61M 2016/0039; A61M 2202/0085; A61M 2202/0208; A61M 2202/0225; A61M 2202/062; A61M 2205/02; A61M 2205/0205; A61M 2205/0238; A61M 2205/15; A61M 2205/18; A61M 2205/3313; A61M 2205/3331; A61M 2205/3584; A61M 2205/3592; A61M 2205/42; A61M 2205/50; A61M 2205/584; A61M 2205/6027; A61M 2205/6045; A61M 2205/6054; A61M 2205/6072; A61M 2205/6081; A61M 2205/70; A61M 2205/75; A61M 2210/1053; A61M 2230/432

See application file for complete search history.

(56) References Cited

U.S. PATENT DOCUMENTS

| | | | |
|---|---|---|---|
| 4,790,306 A | 12/1988 | Braun et al. | |
| 4,883,052 A | 11/1989 | Weiss et al. | |
| 5,097,236 A | 3/1992 | Wakino et al. | |
| 5,481,763 A | 1/1996 | Brostrom | |
| 6,581,594 B1 | 6/2003 | Drew et al. | |
| 6,584,976 B2 | 7/2003 | Japuntich et al. | |
| 6,659,102 B1 | 12/2003 | Sico | |
| 6,662,803 B2 | 12/2003 | Gradon et al. | |
| 6,892,729 B2 | 5/2005 | Smith et al. | |
| 8,353,293 B1* | 1/2013 | Fuhrman | A61M 16/0816 128/204.18 |
| 10,543,333 B2 | 1/2020 | Ng et al. | |
| 2001/0054422 A1 | 12/2001 | Smith et al. | |
| 2005/0056286 A1 | 3/2005 | Huddart et al. | |
| 2006/0278086 A1 | 12/2006 | Inagaki et al. | |
| 2008/0060657 A1 | 3/2008 | McAuley et al. | |
| 2009/0044810 A1 | 2/2009 | Kwok et al. | |
| 2009/0050156 A1 | 2/2009 | Ng et al. | |
| 2009/0272380 A1* | 11/2009 | Jaffre | A61M 16/08 128/205.24 |
| 2010/0239625 A1 | 9/2010 | Puckett | |
| 2012/0285457 A1 | 11/2012 | Mansour et al. | |
| 2012/0285468 A1 | 11/2012 | Birch | |
| 2012/0318270 A1 | 12/2012 | McAuley et al. | |
| 2013/0160769 A1 | 6/2013 | Ng et al. | |
| 2014/0283831 A1 | 9/2014 | Foote et al. | |
| 2017/0065786 A1* | 3/2017 | Stephenson | A61M 16/0683 |
| 2017/0281898 A1 | 10/2017 | Dantanarayana | |

FOREIGN PATENT DOCUMENTS

| | | |
|---|---|---|
| EP | 1912693 | 7/2006 |
| EP | 2051783 | 7/2007 |
| WO | WO 2005/032634 | 4/2005 |
| WO | WO 2011/142678 | 11/2011 |
| WO | WO 2014/015382 | 1/2014 |
| WO | 2015048849 A1 | 4/2015 |
| WO | WO 2016/072868 | 5/2016 |
| WO | WO 2017/160166 | 9/2017 |
| WO | 2018009080 A1 | 1/2018 |
| WO | WO 2018/085889 | 5/2018 |
| WO | WO 2020/053794 A1 | 3/2020 |

* cited by examiner

DIFFUSER FOR A COMPONENT OF A RESPIRATORY THERAPY SYSTEM

BACKGROUND OF THE DISCLOSURE

Field of the Disclosure

The present disclosure generally relates to a diffuser for use with, or comprising part of, a component of a respiratory therapy system, for diffusing gases from a patient interface of the system. This application claims priority from U.S. provisional patent application 62/771,444 filed 26 Nov. 2019, the entire contents of which are hereby incorporated by reference.

DESCRIPTION OF THE RELATED ART

One example of the use of a respiratory therapy system is for the treatment of obstructive sleep apnea (OSA) by continuous positive airway pressure (CPAP) or bi-level positive airway pressure (BiPAP) flow generator systems involving the delivery of pressurized gases to the air-ways of a human via a conduit and a patient interface. Such a patient interface may be any one of the following:
  a) a nasal interface configured to seal around the nares or nose of the patient;
  b) an oral mask configured to seal around the mouth of the patient; or
  c) a full face (or oro-nasal) mask configured to seal around both the mouth and nose of the patient.

Typically, the patient interface creates at least a substantial seal on or around the nose and/or the mouth of a patient. As the patient breathes, carbon dioxide gases from expiration can progressively accumulate in the patient interface, which if left over a period of time, can become hazardous to the patient.

One solution to address or at least alleviate this issue is to provide a washout vent, also known as a bias flow vent, which enables a flow of exhaust gases to be exhausted to the atmosphere from inside the patient interface and which can provide a mechanism for reducing or removing the accumulation of carbon dioxide gases from the patient interface.

The vent, while providing a mechanism for removing carbon dioxide, can also have disadvantages. The vent can sometimes create a disturbance for the patient and/or the patient's bed partner. This disturbance typically manifests itself in two forms: noise and the creation of an air draft.

It has previously been noted that air drafts/airflow can be minimised by spacing individual vent holes of the vent further apart so that there is less entrainment of air and turbulence. At the same time, it can be desirable to reduce the overall size of a patient interface to make it less invasive for the patient and improve comfort. However, a reduced size of patient interface results in less space for vent holes and therefore the spacing between vent holes often needs to be decreased. To try to minimise the size of the patient interface whilst also minimising noise and/or air drafts can be difficult.

Our earlier international patent application WO2018009080, the entire contents of which is incorporated herein by reference, discloses some modification to the vent holes to assist in minimising one or more of the above problems.

It has been previously proposed to provide a diffuser, associated with such a vent, comprising diffuser material having the characteristic of diffusing the vent flow through the bias vent.

The diffuser material may be constructed for example from a non-woven fabric. Non-woven fabrics are a web or matrix of natural or man-made fibres or strands that have been bonded together at various (usually uniformly repeating) locations. This non-woven fabric may be chemically, thermally or mechanically bonded. In one example the fabric may be mechanically bonded using a needle punching process. Needle punched non-woven fabrics are formed by the repeated insertion of barbed needles into the web or matrix of fibres. This 'entangles' multiple fibres of the web or matrix such that at least some of the fibres become twisted or entwined or wrapped or overlapped or connected or bonded together at various regions where the needle(s) is inserted. For ease of reference this phenomenon will be referred to throughout this specification as a mechanical 'bond' or 'interlock'.

It can be a problem that due to excessive wear of the diffuser, either resulting from standard use or cleaning procedures for example, one or more individual fibres of the web or matrix may either sever or become detangled such that the bond or interlock fails. The free end of the or each such fibre may then become somewhat detached from the structure of the diffuser material. In one form this may present itself as 'pilling' which can be detrimental to both the aesthetics and performance of the diffuser.

It is also known to provide an auxiliary vent passage(s). In one example this auxiliary vent passage(s) may be formed between the vent and the diffuser. These auxiliary vent passages serve as a failsafe should the diffuser become blocked and make sure adequate CO2 flushing can occur. A further issue can be that the severed or detangled fibres may be drawn into the path of airflow which could block the vent holes and/or at least partially obstruct any auxiliary vent passage(s). In one example when the diffuser is completely saturated, the piling on the underside of the diffuser retains water and reduces/blocks the auxiliary vent passage. This can be further complicated by the water tension present which further reduces flow. The obstruction of the vent holes and/or auxiliary vent passage(s) may lead to unsuitable flushing of the exhaled gasses from within the patient interface which may provide a severe risk of suffocation to the patient.

SUMMARY OF THE DISCLOSURE

Accordingly, in one aspect the disclosure may broadly be said to consist in a mask assembly for respiratory therapy, comprising:
  a. a vent for exhausting gas flow from an interior of the mask assembly, the vent comprising at least one vent hole;
  b. a diffuser material defining a diffusing area sufficient to cover the at least one vent hole and having a periphery;
  c. wherein a region of the diffusing area of the diffuser material includes a localised joint region in which multiple fibres of the diffuser material are bonded or interlocked together;
  d. and wherein, the location of the localised joint region is offset from the at least one vent hole.

The region of the diffusing area may be a central region of the diffusing material.

The central region may:
  a. extend over a central axis of the vent.
  b. extend radially outwardly from the central axis of the vent, in at least one direction.

c. extend radially outwardly from the central axis of the vent through 360°, when the vent is viewed in a direction substantially along the axis of at least one vent hole.
d. extend in a given direction a distance which is less than 80% of a distance between the central axis and the periphery of the diffuser material, preferably less than 60%, more preferably less than 50% and most preferably less than 40%.
e. occupy an area that is less than 70% of the diffusing area, preferably less than 60%, more preferably less than 50% and most preferably less than 40%.

The diffuser may have a thickness or depth which extends in a direction along the central axis, and the localised joint region may extend through more than 50% of the thickness or depth of the diffuser material.

The localised joint region may extend through the entire thickness of the diffuser material.

The localised joint region may be elongate when viewed in a direction substantially along the axis of at least one vent hole.

The localised joint section may have a shape when viewed in a direction substantially along the axis of at least one vent hole, the shape being selected from any one of:
a. square;
b. rectangular;
c. quadrilateral;
d. circular;
e. elliptical;
f. triangular, or frustro triangular;
g. pentangular;
h. hexagonal.

The vent may comprise an array of vent holes. The array of vent holes may have a shape when viewed in a direction substantially along the axis of at least one vent hole, the diffuser material comprising an array of a plurality of localised joint regions, both arrays comprising substantially the same peripheral shape. The shape may be substantially:
a. trapezoidal;
b. triangular with at least one truncated apex;
c. quadrilateral.

The shape may comprise a pair of sides which incline toward one another, and a top and a base.

Any one or more of the sides, top or base may be substantially straight or include a straight portion.

Any one or more of the sides, top or base may be substantially arcuate or include an arcuate portion.

The shape may be substantially triangular.

The mask assembly may comprise a breathing gas inlet aperture having a diameter or width, the length of the base being less than the diameter or width of the breathing gas inlet aperture.

The or a localised joint region may be aligned with the central axis.

The diffusing area may be sufficient to cover all of the vent holes.

The mask assembly may comprise a plurality of spaced apart localised joint regions. The plurality of localised joint regions may be irregularly spaced apart.

All of the localised joint regions may be offset from the or each vent hole.

The vent may be integrally formed with a mask component of the mask assembly, the diffuser material being mounted on the mask component.

The diffuser material may be permanently attached to the mask component.

The diffuser material may be removably attached to the mask component.

The diffuser material may be attached to a diffuser frame, the diffuser frame being attached to the mask component. The diffuser material may be permanently attached to a diffuser frame. The diffuser frame may be removably attached to the mask component.

The mask component may comprise a mask frame, or a mask body or shell.

The mask assembly may comprise a plurality of vent holes.

The mask assembly may comprise 5 to 15 vent holes.

The plurality of vent holes may be in the range of 8 to 40 holes.

There may be two or more groups or arrays of vent holes.

Each group or array may comprises 16 vent holes.

Each group or array may comprise 32 vent holes.

The mask assembly may comprise a plurality of localised joint regions, wherein the plurality is in the range of 3 to 12, 4 to 10, or 6 to 8.

The mask assembly may comprise a plurality of vent holes and a plurality of localised joint regions, wherein the mask assembly comprises a diffuser ratio being the ratio of the number of vent holes to the number of localised joint regions The diffuser ratio may be less than 10:1, less than 8:1, less than 5:1, or substantially 4.5:1. The diffuser ratio may be 2:1. The diffuser ratio may be in the range of 3 to 6:1.

The diameter, or distance across the localised joint region may be over 0.5 mm, over 0.75 mm, or substantially 1.00 mm. The diameter, or distance across the localised joint region may be less than 2.0 mm, less than 1.5 mm or may be 1.25 mm.

The total cross sectional area of the localised joint region(s) may be between 2 and 10 mm$^2$, may be between 3 and 8 mm$^2$, may be between 4 and 7 mm$^2$, and may be about 6.5 mm$^2$.

The mask assembly may comprise an auxiliary vent formed between the vent and the diffuser material and forming a gases flow path between an interior of the mask assembly and the ambient environment. The auxiliary vent comprises an outlet, the outlet preferably being provided at or near the top of the vent. A direction of gases flow through the auxiliary vent passage is substantially aligned with a longitudinal axis/central plane of the vent, when the vent is oriented in normal use.

The localised joint region may be spaced from the periphery of the diffuser material by a distance between 1 and 20 mm, may be between 4 and 16 mm, and may be between 5 and 12.5 mm.

The mask assembly may comprise a plurality of localised joint regions, arranged in a group or array, wherein the radially outermost localised joint region is less than 5 mm, may be less than 3 mm, and in some examples approximately 2 mm from the periphery of the diffuser material.

The mask assembly may comprise a plurality of spaced apart localised joint regions, wherein the spacing between adjacent localised joint regions is less than 5 mm, may be less than 4 mm and may be less than 3.5 mm.

At least one localised joint region may be spaced from a central plane of the vent. The least one localised joint region may be spaced from a central plane of the vent by between 2 and 10 mm, may be between 2.5 and 7.5 mm, and may be between 3 and 5 mm.

The periphery of the diffuser material may be mounted on a diffuser frame or surround, the diffuser frame or surround being mounted on the mask assembly.

The diffuser frame or surround may comprise a resiliently deformable region which can be resiliently deformed to remove or release the diffuser from the vent or from a position near the vent.

The resiliently deformable region may comprise a raised lip or tab in a discrete region of the diffuser frame or surround.

The underside of the raised lip or tab may be spaced from a surface of the vent.

The raised lip or tab is resiliently deformable such that the raised lip or tab can be elastically deformed towards or away from the auxiliary vent to remove or release the diffuser from the vent.

The elastically or resiliently deformable nature of the lip or tab, and the spacing of the lip or tab from the vent surface, may provide a dual mode release mechanism, which allows a user to select whichever movement is most natural or obvious to release the diffuser from the vent.

The location of the localised joint region may be offset from the periphery of the diffuser material.

The or least one localised joint region may formed from an overmould. The localised joint region may be overmoulded to the diffuser material. The localised joint region may be overmoulded to the diffuser material to space the diffuser from the vent.

In another aspect the disclosure may broadly be said to consist in a mask assembly for respiratory therapy, comprising:
a. a vent for exhausting gas flow including at least two vent holes spaced apart from each other;
b. a diffuser material defining a diffusing area sufficient to cover the at least two vent holes and having a periphery;
c. wherein, a central region of the diffusing area of the diffuser material includes a localised joint region in which multiple fibres of the diffuser material are bonded together;
d. and wherein, the location of the localised joint region is not in the path of the gas flow through the vent holes.

In a further aspect the disclosure may broadly be said to consist in a mask assembly for respiratory therapy, comprising:
a. a vent for exhausting gas flow including at least two vent holes spaced apart from each other;
b. a diffuser material defining a diffusing area sufficient to cover the at least two vent holes, and having a periphery, the periphery having a shape;
c. wherein, a central region of the diffusing area of the diffuser material includes a plurality of localised joint regions in each of which multiple fibres of the diffuser material are bonded together;
and wherein, the plurality of localised joint regions are arranged on the diffuser material such that a notional line bounding all of the localised joint regions has a shape which is substantially identical to the shape of the periphery of the diffuser material.

In another aspect the disclosure may broadly be said to consist in a mask assembly for respiratory therapy, comprising:
a. a vent for exhausting gas flow, the vent comprising:
at least two vent holes spaced apart from each other;
a support rib or land configured to protrude from the vent;
b. a diffuser material defining a diffusing area sufficient to cover the at least two vent holes and having a periphery;
c. wherein a region of the diffuser material is supported by the support rib or land; and
d. wherein, the region of the diffuser material includes a localised joint region in which multiple fibres of the diffuser material are bonded together.

In a further aspect the disclosure may broadly be said to consist in a mask assembly for respiratory therapy, comprising:
a. a vent for exhausting gas flow including at least two vent holes spaced apart from each other;
b. a diffuser material defining a diffusing area sufficient to cover the at least two vent holes and having a periphery;
c. wherein, a central region of the diffusing area of the diffuser material includes a localised joint region in which multiple fibres of the diffuser material are bonded together;
d. the mask assembly further comprising an auxiliary vent passage formed between the vent and the diffuser material and being in communication with both an interior of the mask assembly and the ambient environment.

In one aspect the disclosure may broadly be said to consist in a mask assembly for respiratory therapy, comprising:
a. a vent for exhausting gas flow from an interior of the mask assembly, wherein the vent comprises an array of vent holes spaced apart from each other; the array of vent holes having a shape;
b. a diffuser material defining a diffusing area sufficient to cover the array of vent holes, and having a periphery, the periphery having a shape substantially the same as the shape of the array of vent holes;
c. wherein, a central region of the diffusing area of the diffuser material includes a plurality of localised joint regions in which multiple fibres of the diffuser material are bonded together;
d. and wherein the plurality of localised joint regions includes at least one elongate localised joint region, and a plurality of substantially circular localised joint regions.

In another aspect the disclosure may broadly be said to consist in a diffuser for a mask assembly vent comprising at least one vent hole, the diffuser comprising diffuser material defining a diffusing area sufficient to cover the at least one vent hole and having a periphery;
a. wherein, a region of the diffusing area of the diffuser material includes a localised joint region in which multiple fibres of the diffuser material are bonded together;
b. and wherein, the location of the localised joint region is offset from the at least one vent hole.

In a further aspect the disclosure may broadly be said to consist in a mask assembly for respiratory therapy, comprising:
a. a vent for exhausting gas flow including at least two vent holes spaced apart from each other;
b. a diffuser material defining a diffusing area sufficient to cover the at least two vent holes and having a periphery;
c. wherein, the diffusing area of the diffuser material includes a localised joint region in which multiple fibres of the diffuser material are bonded together; the localised joint region being spaced away from the periphery of the diffuser material;
d. and wherein, the location of the localised joint region is not in the path of the gas flow through the at least two vent holes.

In another aspect the disclosure may broadly be said to consist in a mask assembly for respiratory therapy, comprising:
- a. a vent for exhausting gas flow including at least two vent holes spaced apart from each other;
- b. a diffuser material defining a diffusing area sufficient to cover the at least two vent holes and having a periphery;
- c. wherein, a central region of the diffusing area of the diffuser material includes a localised joint region in which multiple fibres of the diffuser material are bonded together;
- d. the mask assembly further comprising an auxiliary vent passage formed between the vent and the diffuser material and being in communication with both an interior of the mask assembly and the ambient environment; and
- e. wherein the vent has a generally trapezoidal or truncated triangular shape, when viewed from the front of the vent, generally along the axis of the vent holes, having a wider base, and two inclined, opposed, sides which are inclined toward an apex or truncated apex distal from the base.

In one aspect the disclosure may broadly be said to consist in a component of a respiratory therapy system comprising the mask assembly or the diffuser of any one of the above statements.

The mask assembly may comprise any one of:
- a. an elbow connector configured to connect a gas delivery conduit to a patient interface;
- b. a gas delivery conduit;
- c. a mask frame or shroud configured to be connected to headgear;
- d. a gas delivery conduit connector configured to connect a gas delivery conduit to another component of the respiratory therapy system.

In another aspect the disclosure may broadly be said to consist in a respiratory therapy system comprising the mask assembly of any one of the above statements and any one or more of:
- a. a breathing gas flow generator;
- b. a breathing gas humidifier;
- c. a gas delivery conduit, which may or may not be heated; and/or
- d. a patient interface.

The patient interface may be any one of:
- a. a nasal interface configured to seal around the nares or nose of the patient;
- b. an oral mask configured to seal around the mouth of the patient; or
- c. a full face (or oro-nasal) mask configured to seal around both the mouth and nose of the patient.

Further aspects of the disclosure, which should be considered in all its novel aspects, will become apparent from the following description.

DESCRIPTION OF THE DRAWINGS

A number of embodiments of the disclosure will now be described by way of example with reference to the drawings in which.

DETAILED DESCRIPTION OF SPECIFIC EMBODIMENTS

Figure 1:
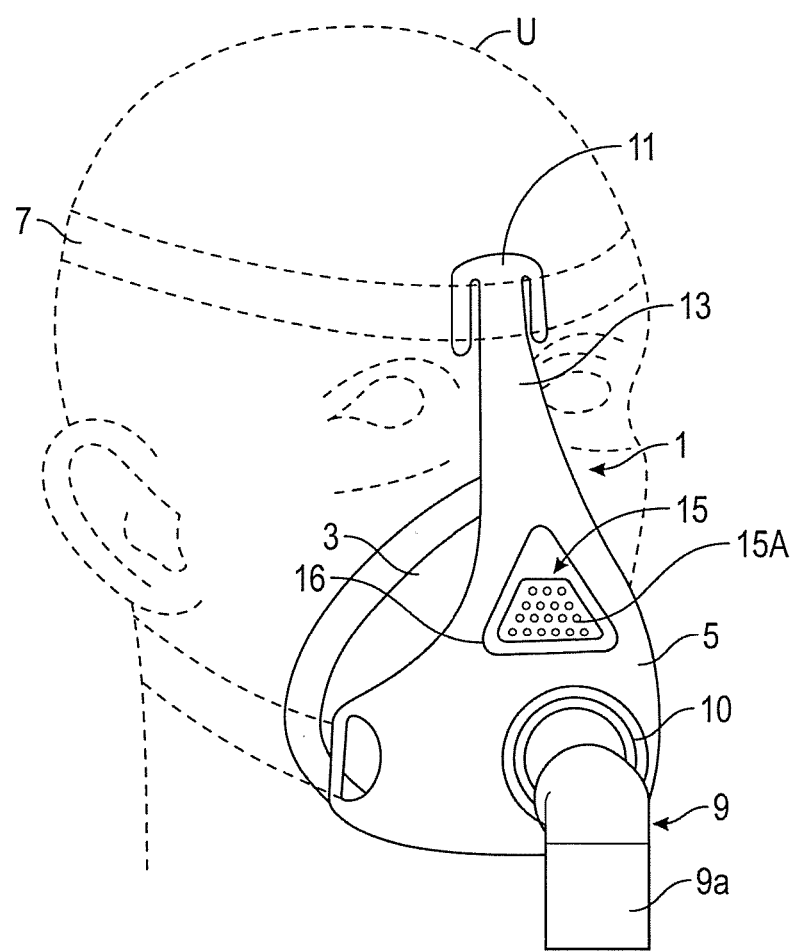
FIG. 1 is a perspective view of a respiratory therapy system component being a patient interface on a patient's head, the patient interface incorporating a vent having a plurality of vent holes/apertures.

With reference initially to FIG. 1, an embodiment of a patient interface 1 is illustrated on a user U, the patient interface 1 incorporating a vent. The interface 1 can be used in the field of respiratory therapy and therefore in any respiratory treatment, respiratory assistance, resuscitation or ventilation system. In some embodiments, the interface 1 has particular utility with forms of positive pressure respiratory therapy. For example, the interface 1 can be used for administering continuous positive airway pressure ("CPAP") treatments, variable positive airway pressure ("VPAP") treatments and/or bi-level positive airway pressure ("BiPAP") treatments. The interface 1 can be compatible with one or more different types of suitable CPAP systems as well as non-invasive ventilation (NIV) systems.

The interface 1 can comprise any of a plurality of different types of suitable mask configurations. For example, certain features, aspects and advantages of the present disclosure can be utilized with nasal masks, oral masks, full face masks, oronasal masks or any other positive pressure mask. Although the illustrated prior art mask is a full face mask, the scope of the present disclosure should not be limited by the particular embodiments described.

In the illustrated configuration, the interface 1 comprises a mask body 3, a mask frame 5 and a connection port assembly 9. The mask body 3 is configured to cover the user's mouth and/or nose to deliver respiratory gases to the user. The mask body 3 can be secured to the mask frame 5. The mask frame 5 is held in place by a headgear assembly 7 that wraps around a part or parts of the user's head. The connection port assembly 9 can be connected to an inlet aperture 10 of the mask body 3 and/or mask frame 5. In some examples this can be achieved with a releasable connection. In some configurations, the connection port assembly 9 can include a ball joint to improve flexibility and comfort. The connection port assembly 9 in this example comprises an elbow connector 9A, which may include a swivel joint such as a ball joint, configured to be connected between the mask body 3 and/or mask frame 5 and a gas delivery conduit (not shown).

The mask frame 5 can couple to the mask body 3 and help stabilize the interface 1 on the user's face. The mask frame 5 can be any shape and size to functionally secure the interface 1 to the user's face. The mask frame 5 may also serve to connect the headgear assembly 7 to the mask body 3. The mask frame 5 can be attached to the mask body 3 with interlocking clips, tabs or other functional couplers and may be releasably or permanently attached. The mask frame 5 can be rigid, substantially rigid or semi-rigid to provide support for the mask body 3. For example, the mask frame 5 can be at least partially made of a metal or rigid plastic, such as acrylic, polycarbonate or high-density polyethylene.

As illustrated in FIG. 1 the mask frame 5 can extend to the user's forehead and may optionally include a forehead rest 11. The forehead rest 11 can help stabilize the interface 1 to the user's face by providing a support point for the interface 1 and connection points for the headgear assembly 7. In the illustrated configuration, a frame bridge 13 extends between the main body of the frame 5 and the forehead rest 11. The frame bridge 13 can be integrally formed or moulded with the rest of the mask frame 5 from the same rigid material.

In some configurations, the forehead rest 11 can be a separate flexible piece that is attached or overmoulded onto the mask frame 5. For example, the forehead rest 11 can be made of a flexible silicone that is overmoulded onto the frame bridge 13. The flexible material advantageously conforms to the user's forehead anatomy and helps improve comfort to the user with soft material contact. In some configurations, the forehead rest 11 can be attached or integrally formed as part of the mask frame 5 and can be made of the same material as the mask frame 5 and frame bridge 13.

The typical method of passively venting carbon dioxide (CO2) and expiratory gases is via the use of a vent comprising a vent hole/aperture or a vent hole/aperture array that is incorporated into the mask body or gas path componentry that, for example, is directly connected to the mask. In the embodiment illustrated in FIG. 1, the interface 1 has a vent 15, which can be a bias vent, for expelling gases from inside the mask to the environment. The vent 15 can help expel carbon dioxide gases from the patient interface that have been exhaled from the user into the patient interface, this reduces the rebreathing of the carbon dioxide gases. In other embodiments, the vent 15 may be provided in the connection port assembly 9, for example on the elbow connector.

The vent 15 creates a controlled or known leak to enable the exhausting of the user's exhaled carbon dioxide gases. There may be a performance trade-off between the location of the vent 15 (relative to the patient's mouth or nose) and the amount of bias flow required. As used herein, bias flow refers to the flow of gases to the environment through the vent holes of the vent. The flow rate of the bias flow and the design geometry of the vent holes can have an effect on the noise level and draft that the bias flow produces, as well as the amount of entrainment that the exiting gas flow may cause, as discussed further below.

In the illustrated configuration, the vent 15 comprises a plurality of vent holes 15A on the mask body 3 that expel gases through a cut-out 16 in the mask frame 5. In other configurations, the vent 15 can comprise slits or larger openings instead of or in addition to small through holes. In some configurations, the vent 15 can be disposed on other portions of the interface, such as the connection port assembly 9 or connection joints, as discussed below. Generally, relatively smaller vent hole sizes produce less airflow noises compared to a larger vent hole size given the same flow velocity through both hole sizes. The plurality of vent holes helps reduce airflow noises compared to having one or a few holes with the same vent area when expelling a given volume of gas.

In some embodiments, the vent 15 can be formed as a separate vent component/module from the mask body 3 or mask frame 5. The separate vent module can be permanently or releasably assembled to the mask body 3 or mask frame 5. For example, the vent module can have threads that mate with complementary threads on the mask body 3. In other configurations, the air vent module can have any type of functional coupler or connector to mate the vent module to the mask body 3 or mask frame 5. The vent module may connect with the mask body 3 or mask frame 5 via a snap fit connection for example, or any other form of interference fit. In these configurations, the vent module can be removed easily for service, cleaning or replacement.

The vent module can be overmoulded to the mask body 3 or mask frame 5 for a permanent attachment. The overmoulding can include a flexible gusset between the vent module and the mask that helps with flexibility. In other configurations, the vent module can be permanently attached using, for example, adhesives, ultrasonic welding or radio-frequency welding.

Furthermore, the vent 15 can be formed of a different material than the mask body 3 or mask frame 5. This can advantageously allow the vent 15 to be made of a material that is more suitable for forming vent holes or apertures. For example, the vent 15 can be made of a soft and/or flexible material while the mask body 3 and/or mask frame 5 are made of a more rigid material. In some configurations, the soft and/or flexible material (e.g., silicone, rubber, foam and the like) may help reduce the amount of noise the flow makes through the vent holes. However, in some embodiments, the vent 15 can be formed of the same material as the mask body 3 and/or mask frame 5 while providing acceptable noise and draft levels. In another configuration the vent 15 can be made of a rigid material while the mask body 3 and/or mask frame 5 are made of a soft and/or flexible material.

A separate vent module can allow improved manufacturing and product quality. By having the vent 15 in a separate component, the moulding of the relatively small and detailed vent holes can be better controlled. By moulding the vent 15 as a separate component, the part tolerances can be better controlled and result in more consistent hole dimensions having a more consistent flow rate performance between parts. Moulding a separate vent module may allow for production of more complex vent designs as a result of not having to accommodate undercuts and other geometric restrictions of other components, such as the mask body 3 for example. Improved control of the part dimensions may also improve control of noise levels, such as by controlling the part contours to produce a smooth air-flow through the vent holes.

Figure 2:
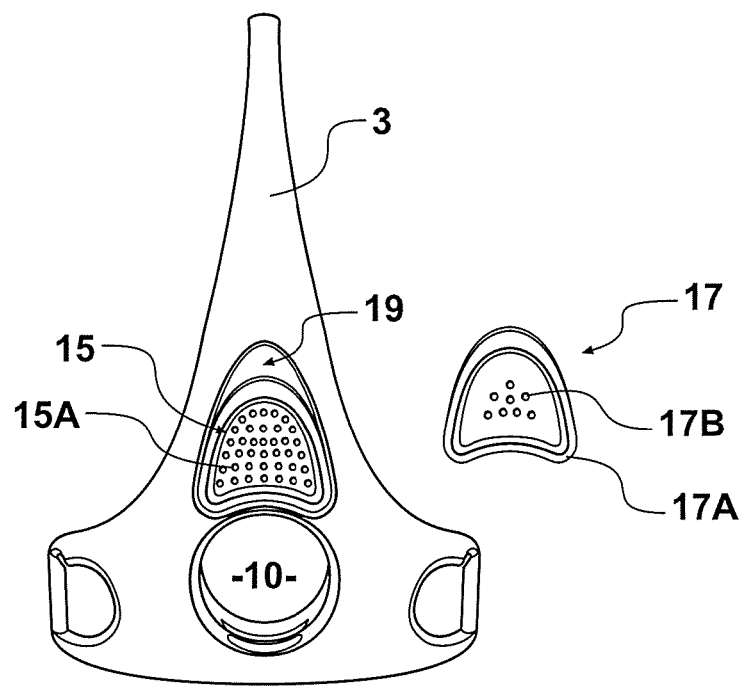
FIG. 2 is a plan view of a mask frame and diffuser in accordance with the present disclosure, in a preassembled condition.
Figure 3:
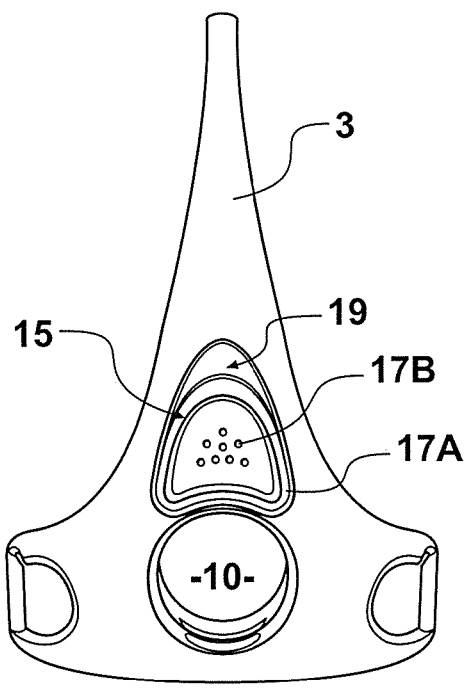
FIG. 3 is a plan view of the mask frame and diffuser of FIG. 2, in an assembled condition.

According to aspects of this disclosure, and with reference to FIGS. 2 and 3, the vent 15, and in particular the or each vent hole 15A can be covered by a diffuser 17 comprising diffuser material.

The vent 15 has a generally trapezoidal or truncated triangular shape, when viewed from the front of the vent, generally along the axis of the vent holes 15A, having a wider base 15B, two inclined sides 15C which are inclined toward one another and meet at a narrower top 15D. In this example:

a) the base 15B and top 15D are arcuate;
b) the base 15B follows the curve of the inlet aperture 10;
c) The sides 15C are substantially straight.

The curve of the base 15B is therefore similar to or complements or mirrors or is parallel to at least a portion of the adjacent curve of the inlet aperture 10, with the remainder of the vent 15 tapering upwardly and inwardly away from the inlet aperture 10, with an apex of the vent 15 being distal from the inlet aperture 10, so that the vent 15 is substantially triangular.

An array of a plurality of vent holes/apertures 15A is provided within the vent base 15B, the vent sides 15C, and the vent top 15D that define the vent area. In this example the vent holes 15A are substantially equispaced and arranged over the area defined by the vent 15. The outermost vent holes 15A follow the shape defined by the vent base 15B, the vent sides 15C, and the vent top 15D.

An auxiliary vent 19 is defined by the profile of the mask frame 5 in the apex region of the vent 15, as is described in more detail below.

The diffuser 17 has a shape and geometry, in particular the shape and geometry of the diffuser periphery, which in this example matches the shape of the vent 15. The vent 15 may be recessed into the mask frame 5, so as to define a recessed region in which the diffuser 17 is inserted, with the outer surface of the diffuser flush with the outer surface of the mask frame 5. In separate embodiments the shape of the diffuser 17 may be different to the shape of the vent 15.

In this example, the diffuser 17 comprises a diffuser frame or support 17A to which the diffuser material 17B is mounted. The outer periphery 17C of the diffuser material 17B may comprise a bonded or interlocked region during manufacture of the diffuser material 17B. For example, the cutting of the diffuser material 17B to the shape required may simultaneously bond the periphery 17C of the diffuser material 17B, via the increased temperature of the cutting tool. The bonded periphery 17C of the diffuser material 17B may be mounted on the diffuser frame 17A using any suitable means, which could be via adhesive or overmoulding for example. In some examples, the diffuser frame 17A may itself be formed by an overmould. In some examples overmoulding the diffuser frame 17A to the diffuser material 17B may form the bonded periphery 17C.

Figure 4:
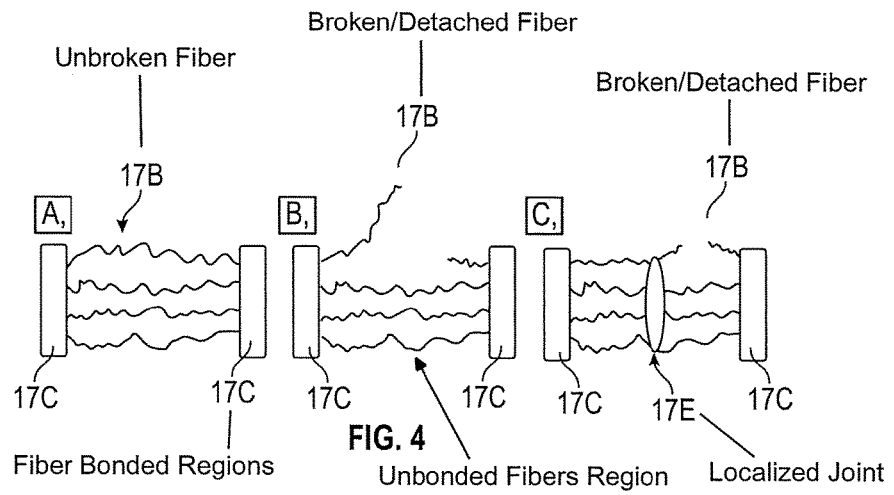
FIGS. 4a-4c are schematic side views of diffuser material.
Figure 5:
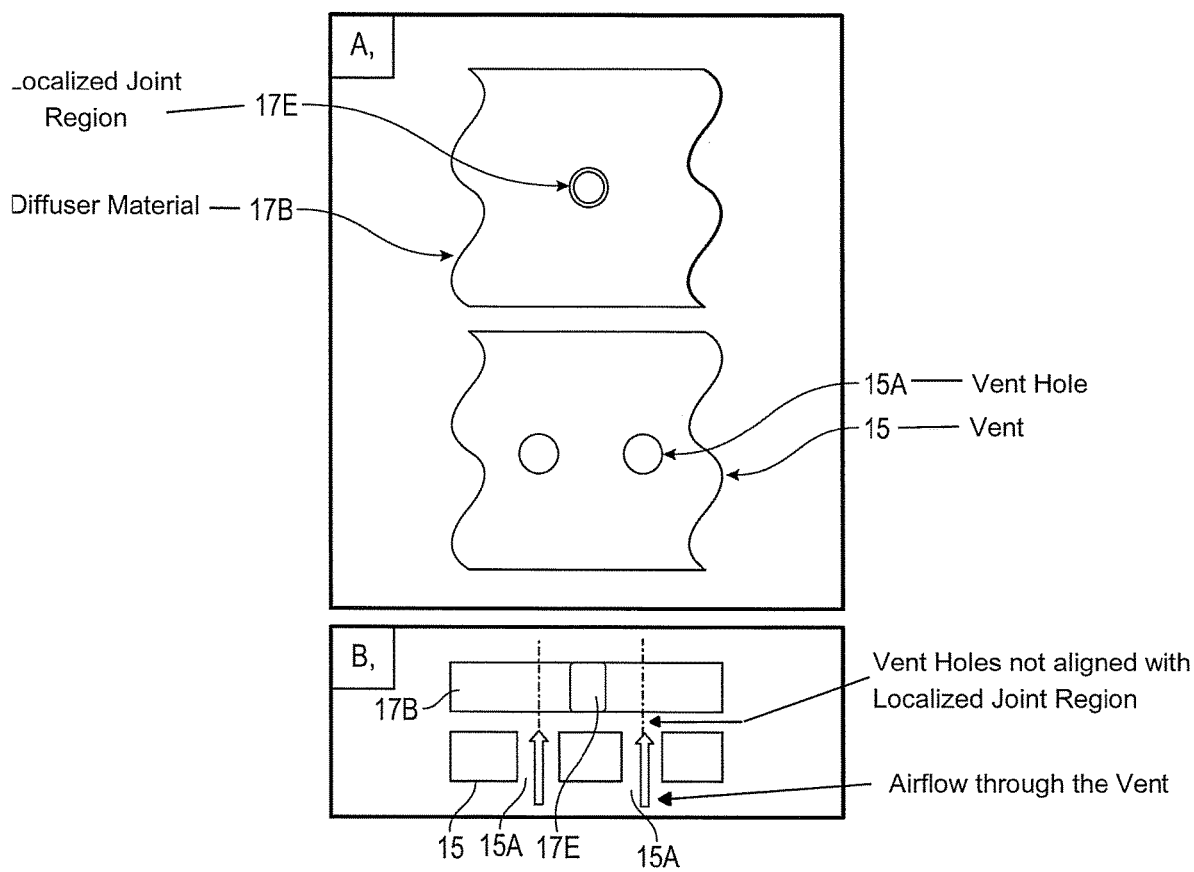
FIGS. 5a and 5b are schematic plan and cross sectional side views of the diffuser of FIGS. 2 and 3.

With additional reference to FIGS. 4 and 5, and as described above, a region or regions of the diffuser material 17B are bonded or interlocked together. In this example, this region is the periphery or margin 17C of the diffuser material. The present disclosure relates to providing additional regions of bonded or interlocked diffuser material, in the area or spaced contained within the periphery 17C. FIG. 4*a* schematically shows lengths of fibre of the diffuser material 17B extending across the diffuser 17 in normal use. FIG. 4*b* shows what can happen to the lengths of fibre in prior art diffusers, when the diffuser material 17B wears or ages or has been used for some time or otherwise deteriorates or becomes damaged.

FIG. 4*c* shows the provision, in accordance with this disclosure, in the diffuser material 17B of at least one localised joint region 17E, between the existing regions of bonded or interlocked diffuser material. The localised joint region 17E comprises a specifically defined and positioned region of the diffuser material 17B which is bonded or interlocked so as to shorten the effective length of at least some of the fibres or strands of the diffuser material 17B, whilst minimising or avoiding any effect on the gas flow performance of the vent 15 and diffuser 17. By effective length, we mean the length of the fibres or strands between localised joint regions, or between a localised joint region and the periphery of the diffuser material.

Though additional needle punched regions could be introduced into the diffuser material manufacturing process to reduce the average length of fibres between the bonded periphery 17C of the diffuser 17, this would lead to detrimental flow performance. Such additional randomly positioned bonded regions would limit airflow through the diffuser material and make it unsuitable for use as a diffuser. It may also undesirably stiffen the diffuser material. Instead, the localised joint regions 17E, which are strategically placed in areas outside of the airflow path(s) through the vent 15 and diffuser 17, achieve the desired result without sacrificing performance. This targeted and irregularly spaced placement of these localised joint regions is unable to be achieved with traditional non-woven mechanical bonding techniques.

With particular reference to FIG. 5, the or each localised joint region 17E is positioned so as not to be aligned with any vent hole 15A in a vertical plane, that is, a plane extending through and perpendicular to the diffuser material, and so not to interfere with the gases flow through any vent hole 15A. In accordance with this disclosure, the arrangement and location of the localised joint region 17E is therefore selected in a predetermined manner. For example:

a) The localised joint region 17E could be positioned in a central location of the vent 15 and diffuser 17 such that the length between un-bonded regions of the maximum number of fibers is reduced.
b) The localised joint regions 17E should not be positioned inline with the vent holes 15A of the vent 15 as this will disrupt airflow and cause undesired restriction through the vent 15, which can lead to excess noise, pressure buildup and/or turbulent flow. This can be achieved by placing the localised joint regions 17E in locations between bias vent holes 15A, or in front of structural components of the bias vent 15 such as ribs, walls, or other structure or mounting locations of the vent 15.

Any one or more of the following properties relating to the localised joint region(s) 17E may be varied or controlled or determined as required:

a) the number of localised joint regions 17E;
b) the size of the or each localised joint region 17E;
c) the shape of the or each localised joint region 17E;
d) the cross-sectional area of the or each localised joint region 17E;
e) the depth of the or each localised joint region 17E, that is, the amount by which the or each localised joint region 17E extends into the diffuser material;
f) the compression of the or each localized joint region 17E, that is the reduction in thickness of the diffuser material that occurs when the localized joint region is formed;
g) the spacing between adjacent localised joint regions 17E;
h) the spacing between the or each localised joint region 17E and the periphery of the diffuser 17;
i) the ratio of the number of localised joint regions 17E to the number of vent holes 15A;
j) the total cross-sectional area of all of the localised joint regions 17E;
k) the ratio of the total cross sectional area of all of the localised joint regions 17E to the total cross sectional area of all of the vent holes 15A;

l) the ratio of the total cross sectional area of all of the localised joint regions 17E to the total cross sectional area of the diffuser material;

m) the shape of a notional line extending around the outside of, and contacting, the outermost localised joint regions 17E may be substantially the same as the shape of the periphery 17C of the diffuser 17.

Figure 11A:
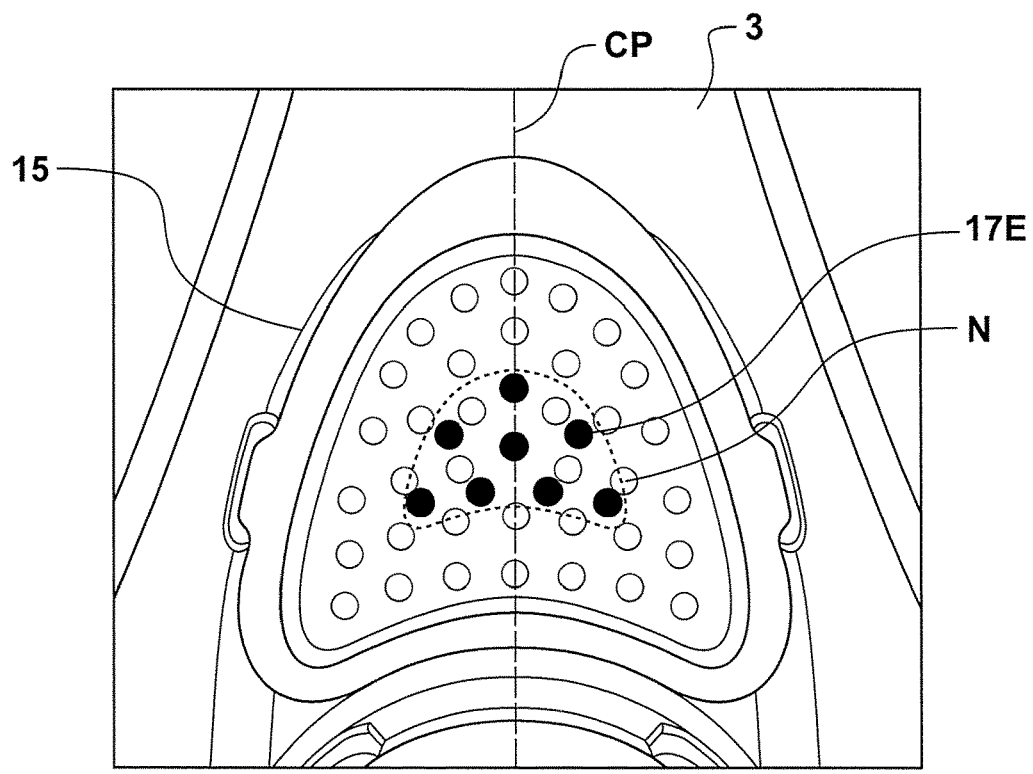
FIGS. 11A, 11B are views corresponding to FIG. 6, showing example notional areas and notional boundaries of the array of localised joint regions.
Figure 11B:
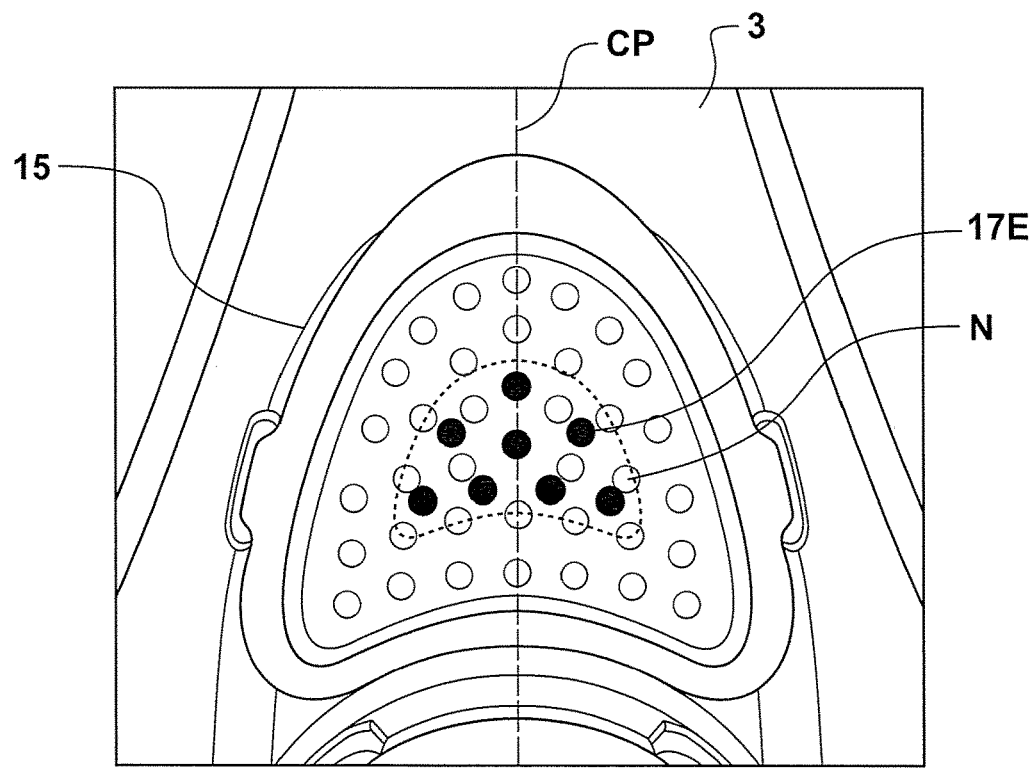

With reference to FIG. 11, two examples of notional boundary lines N, around the array of localised joint regions 17E, are shown. In the example of FIG. 11A, the notional boundary line N contacts the radially outermost margin of each localised joint region 17E and the shape of the array of localised joint regions 17E is defined accordingly. In the example of FIG. 11B, the notional boundary line N is spaced from the radially outermost margin of each localised joint region 17E. In other examples, the notional boundary line could intersect a central axis of each localised joint region 17E, or could contact the radially innermost margin of each localised joint region 17E.

Figure 6:
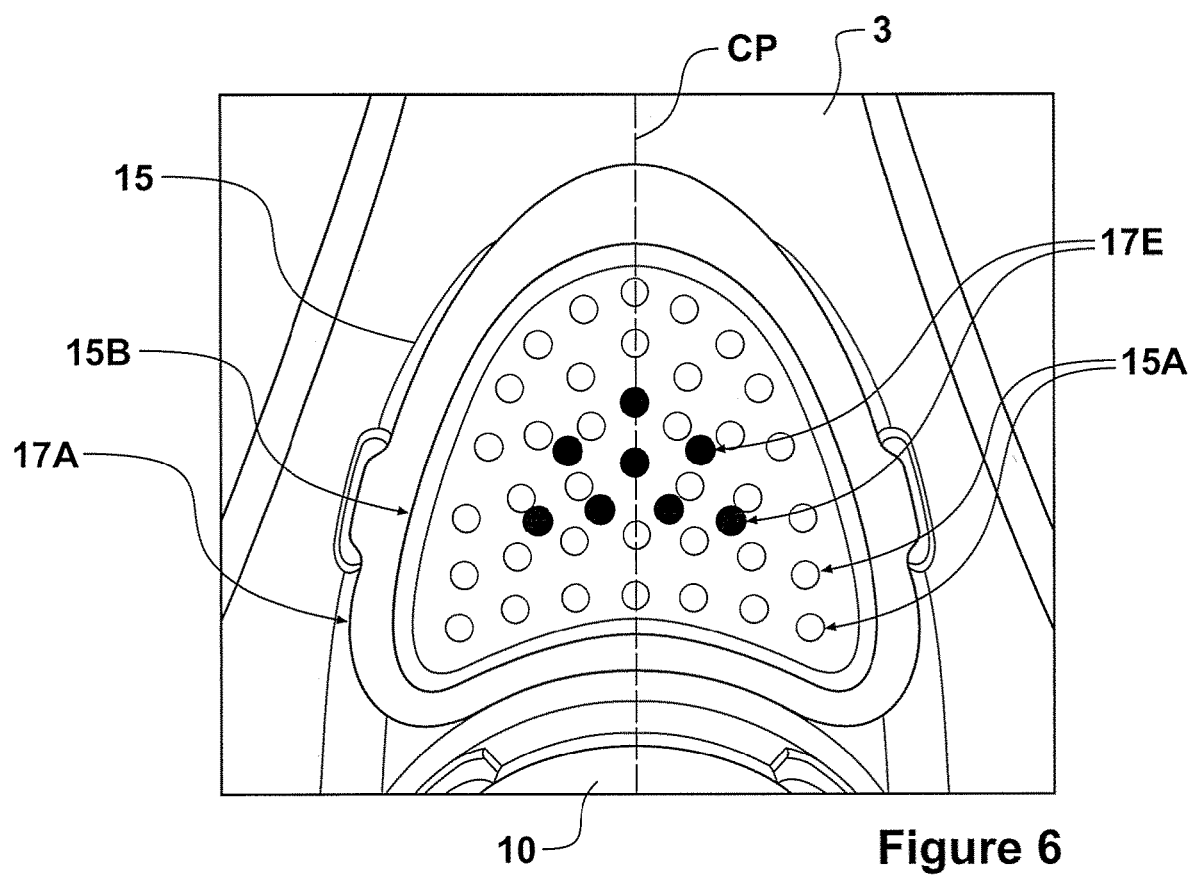
FIG. 6 is a rear view of the vent of the system of FIG. 1 and the diffuser of FIGS. 2 to 5.
Figure 7:
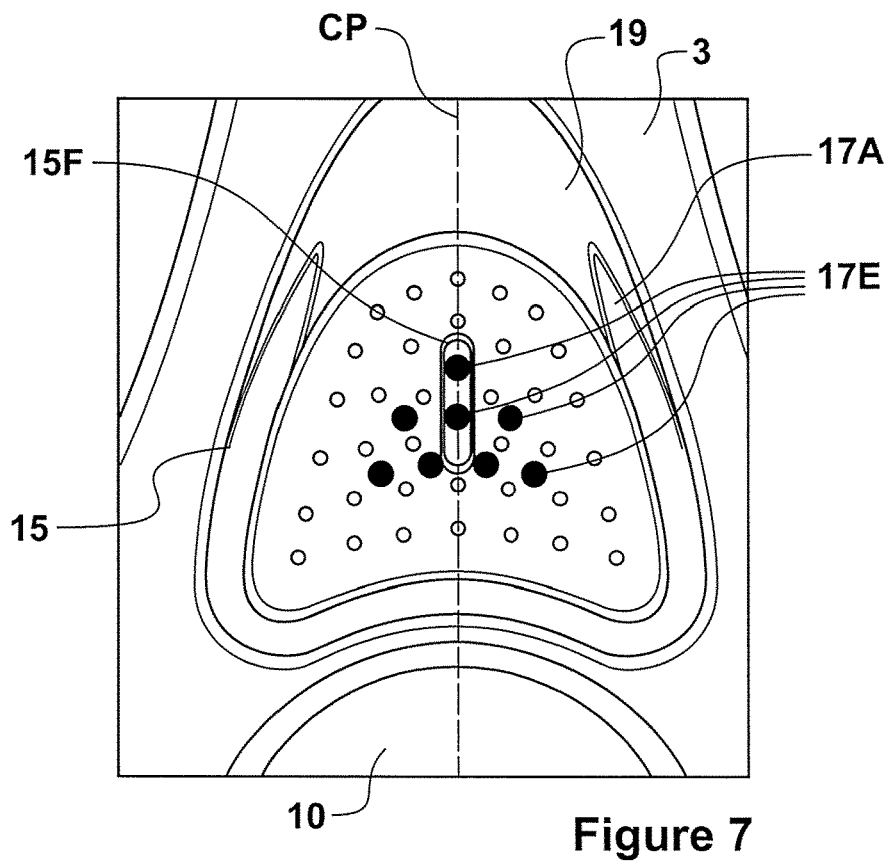
FIG. 7 is an enlarged front view of the vent and part of the mask frame of the system of FIG. 1 and the diffuser of FIGS. 2 to 5.
Figure 8:
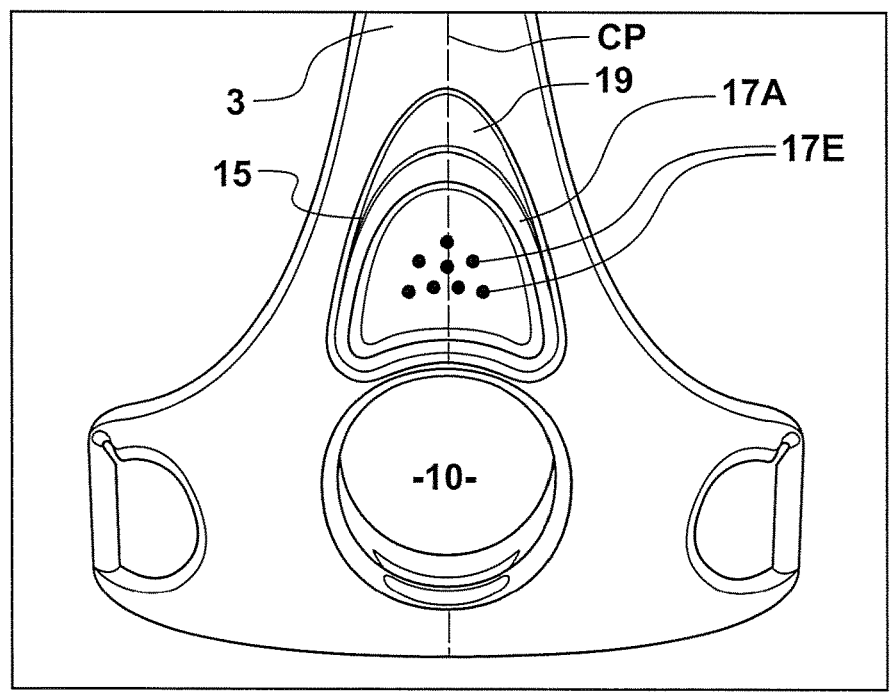
FIG. 8 is a front view of the vent and part of the mask frame of the system of FIG. 1 and the diffuser of FIGS. 2 to 5.

With reference to FIGS. 6 to 8, an example embodiment in accordance with this disclosure is shown, and comprises the following features:

a) Eight localised joint regions 17E on the diffuser 17 and 36 vent holes 15A through the vent 15.

b) The eight localised joint regions 17E are located in a central or centralised or middle region 17F of the diffuser 17.

c) Two localised joint regions 17E are positioned in front of a structure on the vent 15, the structure being in a position where there is no airflow to occlude, and the remaining six localised joint regions 17E are located between various bias vent holes 15A.

In this example, the grouping of the localised joint regions 17E is in a shape that is substantially the same as the shape of the diffuser 17. The shape of the diffuser 17 approximately forms the same shape outline as the localised joint regions 17E.

The diffuser material periphery 17C mechanically bonds all fibers around the perimeter of the diffuser 17. By locating the localised joint regions 17E in a central location the highest, or at least a relatively high, number of fibers are captured and therefore the longest possible, or at least a relatively long, fiber length between bonded regions is reduced with the least additional localised joint regions 17E.

Figure 9:
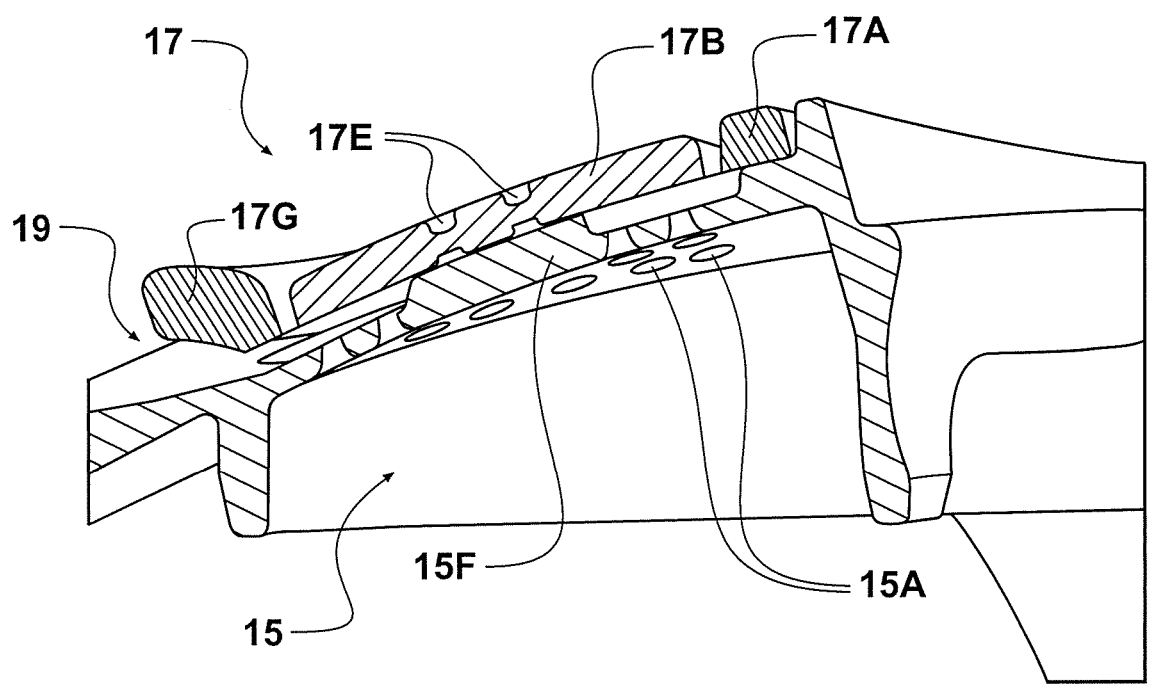
FIG. 9 is an enlarged cross sectional view of the vent and diffuser of FIGS. 1 to 7.

With reference to FIGS. 7 and 9, the vent structure can be more clearly seen, with the localised joint regions 17E shown in shadow behind for clarity. In this example, the vent structure comprises an elongate land or support or rib 15F which projects outwardly from a surface formed by the vent 15. The diffuser material 17B rests on the land or rib 15F which serves to space at least part of the diffuser material 17B from the vent surface. This space forms an auxiliary vent passageway which terminates in the auxiliary vent 19 at the apex of the vent 15. In this example two of the localised joint regions 17E are aligned with, and spaced apart along, the land or rib 15F. As can also be seen from FIGS. 6 and 7, the remaining localised joint regions 17E are located in the spaces between adjacent vent holes 15A.

The auxiliary vent 19 comprises a pathway formed between the vent 15 and diffuser 17 that allows gas to exit from the vent 15 without passing through the diffuser 17 should the diffuser 17 become at least partially occluded. Severed fibers that extend away from the diffuser material 17B and are caught in the gas flow could block this pathway either on their own or in combination with the moisture they retain. The localized joint regions 17E restrict the possible maximum length of the severed fibers and therefore reduce the likelihoods of the auxiliary vent being obstructed. The diffuser 17 is used in a full face mask and if the vent 15 is occluded the dangers of suffocation from excess CO2 are high. The localised joint region(s) 17E overcome or alleviate this issue, noting that in existing nasal masks with a diffuser if the vent or diffuser becomes occluded the patient can always just open their mouth consciously or subconsciously. Although the localised joint regions 17E substantially reduce the issue of the vent being occluded from severed or detached fibers of the diffuser material 17B, it is believed in such a high risk scenario that providing the auxiliary vent 19 additional is beneficial to patient safety. The auxiliary vent 19 is positioned at the apex of the vent 15, and is configured to vent gases generally upwardly and away from the mouth, nose and eyes of the user, and in a direction substantially aligned with the elongate stem of the mask frame 5. The stem of the mask frame 5 thus shields the user from the vented gas, at least to some degree. The general direction or longitudinal axis of the vent passage defined by the auxiliary vent 19 is orthogonal to the central axis of the inlet aperture 10, and aligned with the central plane CP.

With reference to FIG. 9, the cross section is taken through the central plane CP of the mask assembly and as such two of the eight localised joint regions 17E are seen positioned in front of a structural component of the vent 15. Since the area of the diffuser 17 located in front of this structure is already occluded from vent flow it is a preferred location for at least one, and preferably at least some, of the localized joint regions 17E. This is because there will be no additional disruption to the gas flow characteristics while still providing the desired benefits to the diffuser's performance and aesthetics.

With further reference to FIG. 9, the diffuser surround or diffuser frame 17A comprises a resiliently deformable region which forms a raised lip or tab 17G in the region of the auxiliary vent 19. The underside of the raised lip or tab 17G is spaced from the recessed surface of the vent 15 that defines the outlet of the auxiliary vent 19. The raised lip or tab 17G is resiliently deformable such that the raised lip or tab can be elastically deformed towards or away from the auxiliary vent 19. If elastically deformed towards the auxiliary vent 19, the lip or tab 17G pivots the diffuser frame 17A out of the recessed region of the vent 15 in which it sits, to remove the diffuser 17 from the vent 15. If the raised lip or tab 17G is elastically deformed away from the auxiliary vent 19, for example by a user inserting their finger between the underside of the lip or tab 17G and the recessed surface of the auxiliary vent 19, the diffuser 17 can be pulled away from the vent, to remove the diffuser 17 from the auxiliary vent 19. The elastically or resiliently deformable nature of the lip or tab 17G, and the spacing of the lip or tab 17G from the vent surface, provides a dual mode release mechanism, which allows a user to select whichever movement is most natural or obvious to release the diffuser 17 from the vent 15. The lip or tab 17G forms an upwardly inclined, thickened, discrete region of the diffuser surround 17A.

Figure 10:
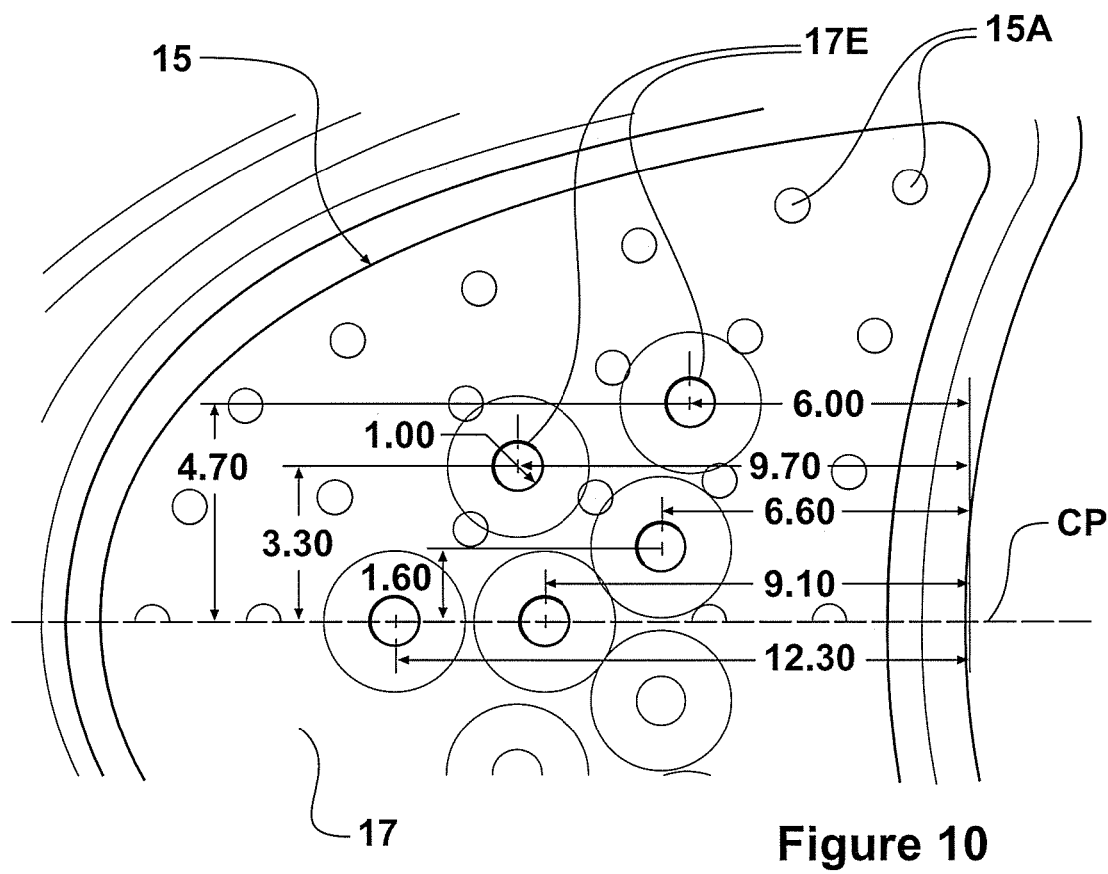
FIG. 10 is an enlarged plan view of part of the vent and diffuser of FIGS. 1 to 8, showing some example dimensions.

With reference to FIG. 10, the location and size of the localized joint regions 17E in accordance with one example are shown. The diameter of each localized joint region is approximately 1.00 mm and therefor the area is approximately 0.79 $mm^2$. In this example, there is an area of approximately 6.32 $mm^2$ of localized joint regions 17E. 'Area' as used herein refers to the area when viewed in a direction along the central plane CP and generally perpendicular to the surface of the vent 15, in a directional along the direction of flow of gases through the vent holes 15A. In some examples the diameter of each localised joint region is in the range of 0.5-2 mm, the area of each localised joint region in the range of 0.3-1.8 mm², and the total area of localised joint regions in the range of 2-10 mm².

In the FIG. 10 example, there are eight localised joint regions 17E arranged in an array of substantially the same shape as the vent array. The localised joint regions 17E are on centres of between 1 and 2 mm, with the localised joint regions 17E being tessellated together with no gap, or only a small gap, between adjacent regions 17E, each localised joint region 17E being offset from the vent apertures 15A, each region 17E being centrally located between three vent apertures 15A. The centres of the regions 17E closest to the lower margin of the vent are between 5.5 and 7 mm from that lower margin. The centre of the region 17E furthest from the lower margin of the vent is between 11 and 13 mm from that lower margin, and in this example 12.3 mm. Other dimensions are shown in FIG. 10, being a distance of a centre of a localised joint region 17E from the lower margin of the vent. The centres of the laterally outermost regions 17E are spaced from the centres of the innermost regions 17E by 4-6 mm, and in this example 4.7 mm. All dimensions shown are examples only. It is envisaged that each dimension shown could vary from the figure shown by +/−0.5, 1, 1.5 or 2 mm approximately.

Figure 12:
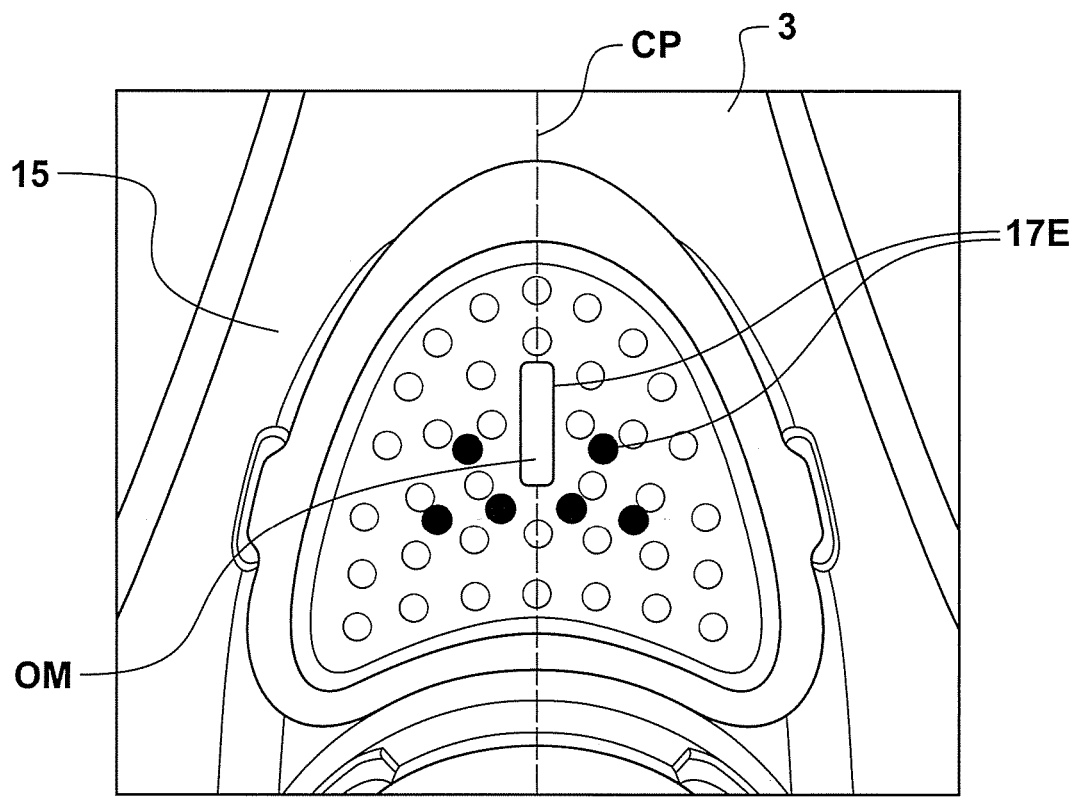
FIG. 12 is an enlarged rear view of a modified vent and diffuser showing overmoulded localised joint regions.
Figure 13:
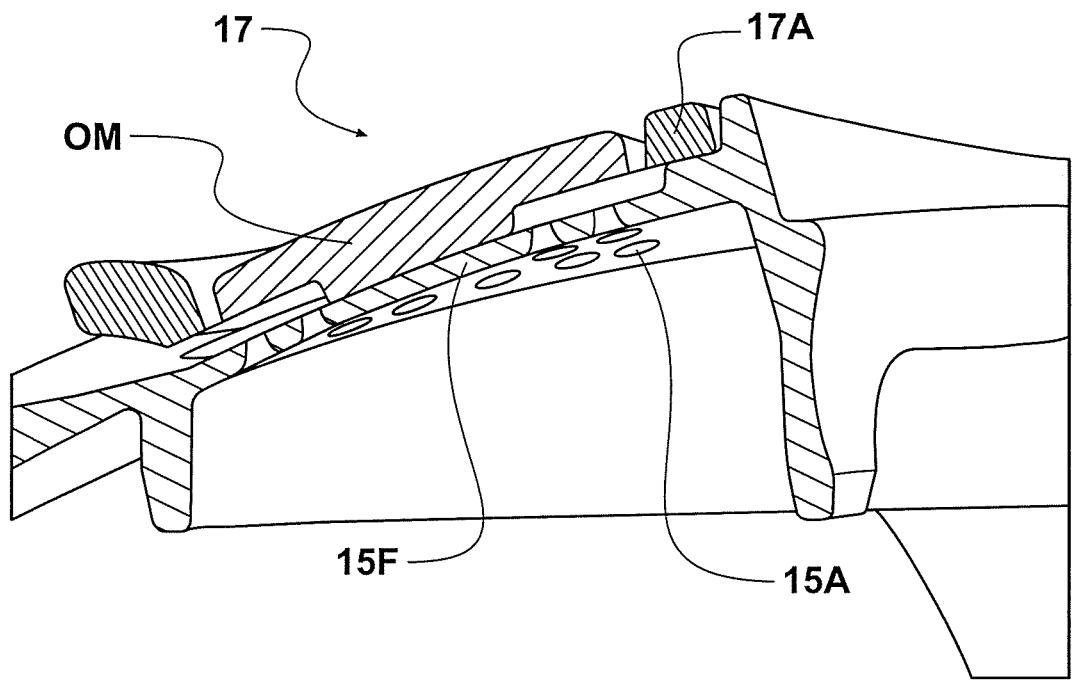
FIG. 13 is a view corresponding to FIG. 9, but showing the overmoulded localised joint regions of FIG. 12.

With reference to FIGS. 12 and 13, in one example a localised joint region 17E can be formed by overmoulding OM, that is, by injecting plastic between the fibres of a region of the diffuser material to entangle them. In this example the localised joint region 17E is central and elongate. Elongate land or rib 15F is overmoulded to the vent 15 so that it joins the diffuser fibres and provides a spacer between the vent and the diffuser. This overmoulding OM and land or rib 15F serves to space the diffuser material from the vent 15, and to entangle the fibres of the localised joint region 17E. The shape of the localised joint region 17E matches the shape of the land or rib 15F.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Where reference is used herein to directional terms such as 'up', 'down', 'forward', 'rearward', 'horizontal', 'vertical' etc., those terms refer to when the apparatus is in a typical in-use position, and are used to show and/or describe relative directions or orientations.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The terms "approximately," "about," and "substantially" as used herein represent an amount close to the stated amount that still performs a desired function or achieves a desired result. For example, in some embodiments, as the context may permit, the terms "approximately", "about", and "substantially" may refer to an amount that is within less than or equal to 10% of, within less than or equal to 5% of, and within less than or equal to 1% of the stated amount.

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

The invention claimed is:

1. A mask assembly for respiratory therapy, comprising:
a vent for exhausting gas flow from an interior of the mask assembly, the vent comprising at least one vent hole;
a diffuser material defining a diffusing area sufficient to cover the at least one vent hole and having a periphery;
wherein a region of the diffusing area of the diffuser material includes a localised joint region in which multiple fibres of the diffuser material are bonded or interlocked together;
and wherein, the location of the localised joint region is offset from the at least one vent hole.

2. The mask assembly of claim 1 wherein the region of the diffusing area is a central region of the diffusing material.

3. The mask assembly of claim 2 wherein the central region extends over a central axis of the vent.

4. The mask assembly of claim 3 wherein the central region extends radially outwardly from the central axis of the vent through 360°, when the vent is viewed in a direction substantially along the axis of at least one vent hole.

5. The mask assembly of claim 1, wherein the diffuser material has a thickness or depth which extends in a direction along a central axis of the vent, the localised joint region extending through more than 50% of the thickness or depth of the diffuser material.

6. The mask assembly of claim 1, wherein the diffuser material has a thickness or depth which extends in a direction along a central axis of the vent, the localised joint region extends through the entire thickness of the diffuser material.

7. The mask assembly of claim 1, wherein the localised joint region is elongate when viewed in a direction substantially along the axis of at least one vent hole.

8. The mask assembly of claim 1, wherein the localised joint section has a shape when viewed in a direction substantially along the axis of at least one vent hole, the shape being selected from any one of:
   a. square;
   b. rectangular;
   c. quadrilateral;
   d. circular;
   e. elliptical;
   f. triangular;
   g. pentangular;
   h. hexagonal.

9. The mask assembly of claim 1, wherein the vent comprises an array, the array comprising a plurality of vent holes.

10. The mask assembly of claim 9 wherein the diffusing area is a sufficient size to cover all of the vent holes in the array.

11. The mask assembly of claim 9 wherein the plurality of vent holes is in the range of 8 to 40 holes.

12. The mask assembly of claim 1, comprising a plurality of spaced apart localised joint regions.

13. The mask assembly of claim 12 wherein the plurality of localised joint regions are irregularly spaced apart.

14. The mask assembly of claim 12 wherein all of the localised joint regions are offset from the or each vent hole.

15. The mask assembly of claim 1, when the vent is integrally formed with a mask component of the mask assembly, the diffuser material being mounted on the mask component.

16. The mask assembly of claim 15 wherein the diffuser material is permanently attached to the mask component.

17. The mask assembly of claim 15 wherein the diffuser material is removably attached to the mask component.

18. The mask assembly of claim 15, wherein the diffuser material is attached to a diffuser frame, the diffuser frame being attached to the mask component.

19. The mask assembly of claim 18 wherein the diffuser material is permanently attached to the diffuser frame.

20. The mask assembly of claim 1, comprising a plurality of localised joint regions, wherein the plurality is in the range of 3 to 12, 4 to 10, or 6 to 8.

21. The mask assembly of claim 1, wherein the multiple fibres of the localised joint region are bonded together.

22. The mask assembly of claim 21, wherein the localized joint region is formed by a material overmolded onto the diffuser material.

23. The mask assembly of claim 1, wherein the diffuser material is a non-woven material.

* * * * *